United States Patent [19]

Grossman

[11] 4,161,945

[45] Jul. 24, 1979

[54] SELECTIVE INTERFERENCE FILTER

[75] Inventor: Hyman Grossman, Elmwood Park, N.J.

[73] Assignee: Cambridge Instrument Company, Inc., Ossining, N.Y.

[21] Appl. No.: 844,896

[22] Filed: Oct. 25, 1977

[51] Int. Cl.² .............................................. A61B 5/04
[52] U.S. Cl. ..................................... 128/696; 128/901
[58] Field of Search ..................... 128/2.06 B, 2.06 F, 128/2.06 G, 2.06 R; 328/114, 115, 116, 117, 154, 165, 167

[56] References Cited

U.S. PATENT DOCUMENTS

| 3,375,451 | 3/1968 | Borelli et al. | 328/167 |
| 3,453,486 | 7/1969 | Weber | 128/2.06 R |
| 3,534,282 | 10/1970 | Day | 128/2.06 B |
| 3,767,939 | 10/1973 | Chamran et al. | 328/167 |
| 3,811,428 | 5/1974 | van Horn et al. | 128/2.06 B |

Primary Examiner—William E. Kamm
Attorney, Agent, or Firm—Eugene E. Geoffrey, Jr.

[57] ABSTRACT

Filtering means for biophysical recording apparatus for removing interference from a signal source which includes a band rejection or notch filter and means for inserting the filter into the signal circuit when the signals have a certain characteristic and for removing the filter when the signals have another characteristic.

6 Claims, 7 Drawing Figures

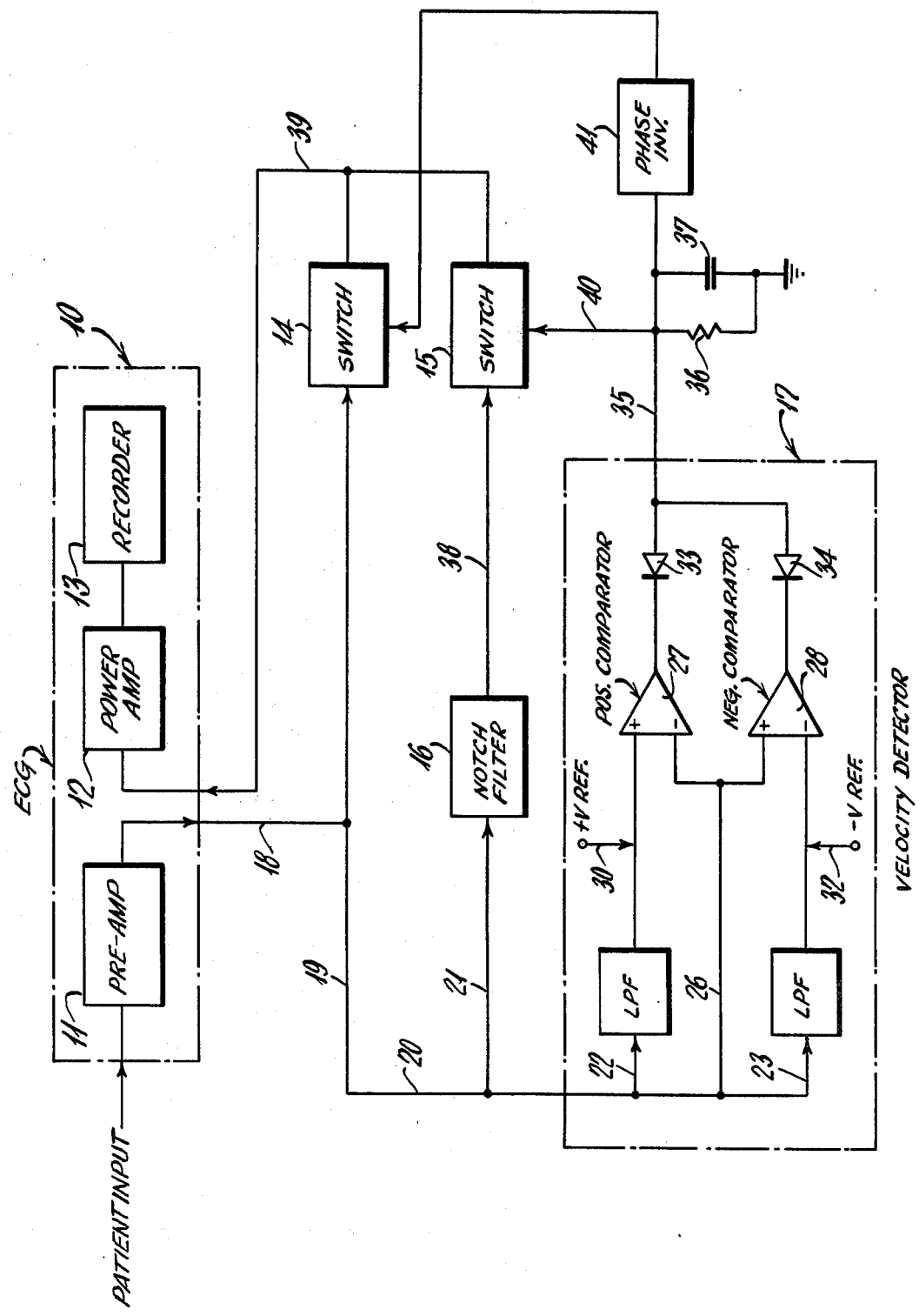

SELECTIVE INTERFERENCE FILTER

This invention relates to apparatus for processing electrical signals such as signals produced by electrocardiographs and similar devices for recording biological and other signals and more specifically to a novel and improved filter and associated circuitry for enhancing the quality of recordings through the elimination of interference such as that produced by power line hum and in the case of electrocardiographs somatic muscle tremor.

In the recording of biological signals such as the electrocardiographic signals both slowly varying components of small amplitude as well as rapidly varying components of significantly greater amplitude are involved. Power line hum and somatic muscle tremor are of low amplitude and high frequency and accordingly tend to obscure the slowly varying components of the electrocardiographic signal. They have relatively little effect however, on rapidly varying signals of substantially larger amplitude. The novel and improved interference filter in accordance with the invention is arranged to discriminate against high frequency low amplitude signals which occur during the slowly varying portion of the recorded signal and is automatically inactivated during the rapidly varying components of the signal so that the latter can be recorded without the loss of any clinical information.

Another object of the invention resides in the provision of a recorder for biological signals which embodies a novel and improved interference filter for selectively removing low amplitude high frequency interference during portions of the recorded signal which are of low frequency and small amplitude.

A further object of the invention resides in the provision of a novel and improved selective interference filter for use in combination with recording devices for biological signals such as electrocardiographs and the like.

The objects of the invention are attained by a filtering system which utilizes circuitry for identifying rapidly varying signals and this circuitry is interconnected with a filter such as a notch filter tuned generally to the power line frequency so that the notch filter will continuously remove power line interference as well as interference produced by somatic muscle tremor during periods when the recorded signal has low amplitude low frequency variations. When the signal starts to vary rapidly the velocity detector inactivates the notch filter so that the signal is recorded independently of any filtering action.

The above and other objects of the invention will become more apparent from the following description and accompanying drawing which constitutes essentially a block diagram of recording apparatus and filtering means for removing undesirable interference.

Referring now to the drawings a biological signal recorder such as an electrocardiograph is generally noted by the numeral 10 and comprises a pre-amplifier 11, a power amplifier 12 and a recorder 13. The design and construction of these elements of an electrocardiograph are well known in the art and a detailed description is not considered necessary. It will be observed however, that the selective interference filter in accordance with the invention is interposed between the pre-amplifier 11 and the power amplifier 12 as it is desirable to treat the signal at a reasonable level but prior to amplification by the power amplifier which is utilized to drive a suitable recorder.

The filter in accordance with the invention comprises, in the illustrated embodiment, two switches 14 and 15, a notch filter 16 and a velocity detector 17. The velocity detector 17, as will be described, normally functions to operate the switches 14 and 15 alternately to either connect the pre-amplifier 11 directly to power amplifier 12 or the output of the pre-amplifier 11 through the notch filter 16 to the power amplifier 12. Thus, the notch filter will function to filter the signal during low frequency or low amplitude portions of the signal being recorded and will be inactivated during periods of large rapid variations in the recorded signal.

More specifically, the output of pre-amplifier 11 is fed through conductors 18, 19, 20 and 21 to the notch filter 16 and through conductors 22 and 23 to a pair of low pass filters 24 and 25 respectively. The signal is also fed through a conductor 26 to amplifiers 27 and 28 which function as positive and negative comparators respectively. The low pass filter 24 is connected through a conductor 29 to the positive comparator amplifier 27 which is also provided with a positive reference voltage fed to the conductor 29 by an input lead 30. Similarly, the output of the low pass filter 25 is fed to the negative comparator amplifier 28 through a conductor 31 which has a negative reference voltage applied through the lead 32. Thus, each comparator compares the signal from the pre-amplifier with that same signal after passing through a low pass filter with the result that amplifier 27 will be driven negative during a rapidly varying positive excursion of the signal while the amplifier 28 will be driven negative during a rapidly varying negative excursion. The outputs of these amplifiers are connected through diodes 33 and 34 to a common conductor 35 having a resistor 36 and a condenser 37 connected in parallel between it and ground. Thus, the outputs of the amplifiers 27 and 28 are summed and applied to resistor 36 and condenser 37.

With the foregoing arrangement the condenser 37 will be charged to a fairly large negative voltage during the presence of a rapidly varying signal and after the signal has ceased it will then discharge at a somewhat slower rate than the charging rate to prevent the introduction of the notch filter at the peak of a large wave as will be described.

The notch filter 16, which may take any desirable configuration such as a parallel-T filter or the like, is connected via the lead 38 to the switch 15 and the output of switch 15 is connected through the lead 39 to the power amplifier 12. The switch 15 is operated directly from conductor 35 by means of the lead 40, so that in the absence any signal on lead 35 the switch 15 will be in the "on" or "conducting" position and connect the notch filter between the output of the pre-amplifier 11 and the input of power amplifier 12. At the same time, the switch 14 will be in the "off" or "non-conducting" position to avoid interference with the action of the notch filter. Should the signal from the pre-amplifier suddenly increase in amplitude, the velocity detector will produce a negative output voltage and rapidly charge condenser 37. This will put a large negative voltage on the switch 15 switching it to the "non-conducting" or "off" position. At the same time this large negative voltage will be processed by the phase inverter and remove the large negative signal normally present on the switch 14 and cause it to shift to the "on" or "conducting" position so that the signal from the pre-amplifier will be fed directly to the input of the power amplifier 12. In this way, the distortion produced by the notch filter on rapidly varying components of the signal will not be present and yet shortly after the signal returns to it original state the notch filter will again be switched into the circuit to remove the undesirable interference.

In actual practice it has been found that hum produced by the power line frequency can be reduced approximately 100 times or to a level about −40 dB. Material reduction of interference produced by the somatic muscle tremor will also be effected. In addition, it has been found that the time constant of resistor 36 and condenser 37 is preferably adjusted to about 20 milliseconds to prevent any sudden switching from occurring at the peak of a rapidly varying wave.

In actual tests conducted with the selective interference filter in accordance with the invention and interconnected with an electrocardiograph it has been found that the various portions of the signals produced by heart action namely, the QRS complex and the P and T waves will all pass the filter undisturbed, and further the delay introduced to prevent reinsertion of notch filter insures an accurate reproduction of all of the essential portions of the electrocardigraphic signal and at the same time, the delay allows any ringing that may have resulted from the action of the notch filter on a rapidly varying signal such as the QRS complex to settle before the filter is reintroduced to the signal path.

While only one embodiment of the invention has been illustrated and described it is apparent that alterations, changes and modifications may be made without departing from the true scope and spirit thereof.

What is claimed is:

1. Filtering apparatus for electrical signals produced by biophysical recording apparatus such as an ECG comprising a notch filter having an input and output, means for feeding said signals to the input of said notch filter, a velocity detector having an input connected to said notch filter and including means for producing control signals in response to the presence and absence of a rapid rate of change of first said electrical signal, switch means interconnected between the input and output of said notch filter and with said velocity detector whereby one of said control signals will actuate said switch means to selectively feed said electrical signals through said notch filter and the other of said control signals will actuate the switch means to bypass said filter, and means for delaying reinsertion of said notch filter after it has been bypassed.

2. Filtering apparatus according to claim 1 wherein said switch means comprises a first switch connected in series with said notch filter and a second switch connected in parallel with the series connected notch filter and the first said switch and said velocity detector is connected to both said switches whereby one control signal will open one switch and close the other and the other control signal will open said other switch and close said one switch.

3. Filtering apparatus according to claim 1 wherein said velocity detector comprises a pair of low pass filters each having an input and output with the input being connected to the input of the velocity detector, a positive comparator having inputs connected to the input and output of one low pass filter, a negative comparator having inputs connected to the input and output of the other low pass filter, said comparators having outputs coupled one to the other, the positive comparator producing a negative control signal in response to a signal having a rapidly varying positive excursion and the negative comparator producing a negative control signal in response to a signal having a rapidly varying negative excursion, said comparators producing substantially zero voltage control signals in the absence of input signals to said detector having rapidly varying excursions whereby said negative control signal will actuate said switches to bypass said notch filters and said zero control signal will actuate said switches to reinsert said notch filter.

4. Filtering apparatus according to claim 3 wherein said delaying means comprises a capacitor and resistor connected in parallel and connected to the combined outputs of said comparators whereby the capacitor is charged negatively in response to the presence of the negative control signal and slowly discharges after termination of said negative control signal.

5. Filtering apparatus according to claim 4 wherein said switch means comprises a first switch connected in series with said notch filter and a second switch connected in parallel with the series connected notch filter and the first said switch and said velocity detector is connected to both said switches whereby one control signal will open one switch and close the other and the other control signal will open said other switch and close said one switch.

6. Filtering apparatus according to claim 1 wherein said notch filter is tuned to remove power line interference.

* * * * *